United States Patent [19]

Muntwyler et al.

[11] 4,364,949
[45] Dec. 21, 1982

[54] HYDROXYPHENYL KETONES

[75] Inventors: René Muntwyler, Hofstetten; Raphael Menassé, Münchenstein, both of Switzerland

[73] Assignee: Ciba-Geigy Corporation, Ardsley, N.Y.

[21] Appl. No.: 214,825

[22] Filed: Dec. 10, 1980

[30] Foreign Application Priority Data

Dec. 21, 1979 [CH] Switzerland ............... 11401/79

[51] Int. Cl.³ ............... C07D 213/64; A61K 31/44
[52] U.S. Cl. ............... 424/263; 546/261; 546/300; 546/301; 546/302
[58] Field of Search ............... 546/301, 302, 261, 300; 424/263

[56] References Cited

U.S. PATENT DOCUMENTS

| | | | |
|---|---|---|---|
| 3,295,946 | 1/1967 | D'Amico | 71/94 |
| 3,772,307 | 11/1973 | Kaminsky et al. | 546/294 |
| 3,862,305 | 1/1975 | Bouillon et al. | 424/45 |
| 4,041,033 | 8/1977 | Douglass | 544/239 |
| 4,048,181 | 9/1977 | Douglass | 546/292 |
| 4,050,921 | 9/1977 | Plant et al. | 71/76 |
| 4,120,692 | 10/1978 | Plant et al. | 71/94 |

*Primary Examiner*—Alan L. Rotman
*Attorney, Agent, or Firm*—Edward McC. Roberts

[57] ABSTRACT

Hydroxyphenyl ketones of the formula:

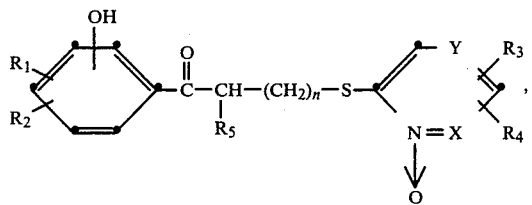

in which n is 0, 1, 2 or 3, X is C or N and Y is C, N or N→O, the heterocyclic structure containing not more than 2 N atoms as ring members, $R_1$ and $R_2$ are each H, F, Cl, Br, $NO_2$, $CH_3$ or $OCH_3$, $R_3$ is H, Cl, Br, $NO_2$, CN, $CH_3$, $OCH_3$, $NH_2$ or $NHCOCH_3$ and $R_4$ is H, Cl, Br or $CH_3$ or together with $R_3$ is a benzene ring fused at the bond [b], if X is C, and $R_5$ is hydrogen or a group of the formula

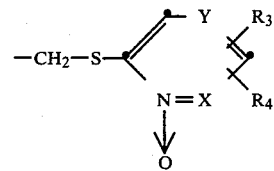

if n=1. Processes for the preparation of these compounds are also proposed. The said compounds can be used to control harmful micro-organisms.

10 Claims, No Drawings

HYDROXYPHENYL KETONES

The present invention relates to novel hydroxyphenyl ketones which contain a 1-azaaryl-2-thio-1-oxide group, processes for their preparation, antimicrobial compositions containing these ketones and the use of the novel compounds for the control of microorganisms.

Diverse pyridine N-oxides which in the 2-position contain a thiol group, or an alkyl, aralkyl or arylthio group which can be further substituted, and which have an antimicrobial action have been disclosed in the literature. In this context see, for example, U.S. Pat. Nos. 3,295,946 and 4,048,181 and German Offenlegungsschrift No. 2,165,752.

U.S. Pat. No. 3,772,307 discloses, inter alia, pyridyl-N-oxide-2-thio-phenyl ketones, which can be used as fungicidal and bactericidal active compounds.

It has now been found, surprisingly, that a specific group of 1-azaaryl-1-oxide-2-thiohydroxyphenyl ketones have a particularly good antimicrobial action against Gram-positive and Gram-negative bacteria, fungi and yeasts and, in respect of the intensity of this action, are superior to the known compounds of similar constitution which have been mentioned, and, at the same time, have a very broad spectrum of action. In addition, the novel compounds according to the invention have a lower toxicity than comparable compounds.

The hydroxyphenyl ketones according to the invention have the formula:

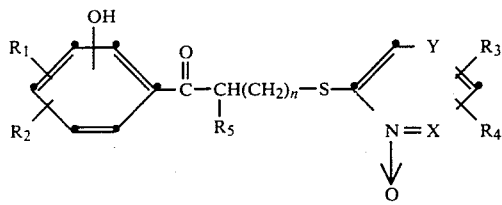

(1)

in which n is the number 0, 1, 2 or 3, it being possible for the hydroxyl group to be in the 3-position only when n is 0 or 1, X is a carbon atom or nitrogen atom and Y is a carbon atom or nitrogen atom or a $\geq N \rightarrow O$ group, but the heterocyclic ring cannot contain more than 2 nitrogen atoms as ring members, $R_1$ and $R_2$ independently of one another are hydrogen, fluorine, chlorine, bromine, nitro, methyl or methoxy, $R_3$ is hydrogen, chlorine, bromine, nitro, cyano, methyl, methoxy, amino or $-NHCOCH_3$ and $R_4$ is hydrogen, chlorine, bromine or methyl, or, if X is a carbon atom, $R_3$ and $R_4$ together are the member required to complete a benzene ring fused at bond [b] of the heterocyclic ring, and $R_5$ is hydrogen or, if n is 1, a group of the formula:

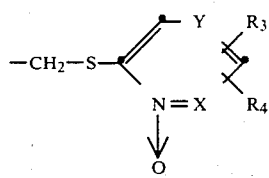

(1a)

in which $R_3$, $R_4$, X and Y are as defined above.

If $R_3$ and $R_4$ together are a benzene ring fused at [b], a heterocyclic group of the formula:

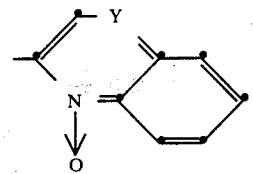

results in which Y is a carbon atom, a nitrogen atom or the $\geq N \rightarrow O$ group.

Preferred compounds of the formula (1) are the compounds of the formula:

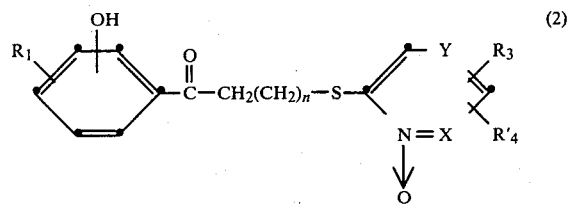

(2)

in which n, X, Y, $R_1$ and $R_3$ are as defined under formula 1 and $R_4'$ is hydrogen or, if X is a carbon atom, together with $R_3$ is the member required to complete a benzene ring fused at bond [b] of the heterocyclic ring, and compounds of the formula:

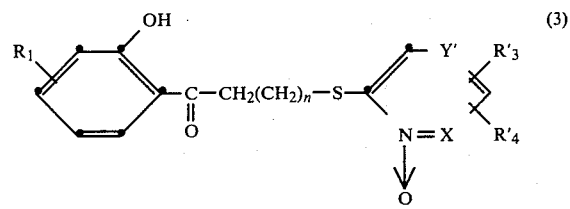

(3)

in which n, $R_1$ and X are as defined under formula 2 and Y' is a carbon atom or nitrogen atom, $R_3'$ is hydrogen, chlorine, bromine or methyl and $R_4'$ is hydrogen, or, if X is a carbon atom, $R_3'$ and $R_4'$ together are the member required to complete a benzene ring fused at bond [b] of the heterocyclic ring.

Compounds of particular importance in practice are those of the formula:

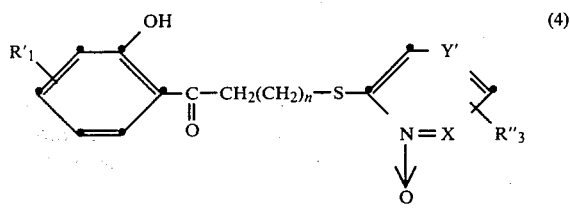

(4)

in which n is the number 0, 1, 2 or 3, X and Y' independently of one another are a carbon atom or a nitrogen atom, $R_1'$ is hydrogen, chlorine, bromine, nitro or methyl and $R_3''$ is hydrogen, chlorine, bromine or methyl, and especially those of the formula (4) in which $R_1'$ is hydrogen, chlorine or methyl and $R_3''$ is hydrogen, chlorine or methyl.

Further compounds worthy of particular mention are those of the formula:

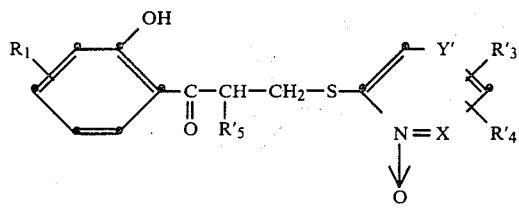 (5)

in which $R_1$ and X are as defined under formula 1 and Y' is a carbon atom or nitrogen atom, $R_3'$ is hydrogen, chlorine, bromine or methyl and $R_4'$ is hydrogen, or, if X is a carbon atom, $R_3'$ and $R_4'$ together are the member required to complete a benzene ring fused at bond [b] of the heterocyclic ring, and $R_5'$ is hydrogen or a group of the formula:

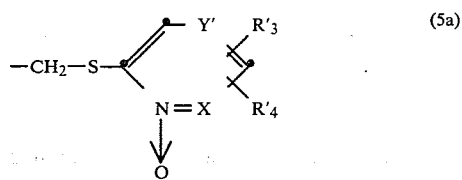 (5a)

in which $R_3'$, $R_4'$, X and Y' are as defined above, and in particular those of the formula:

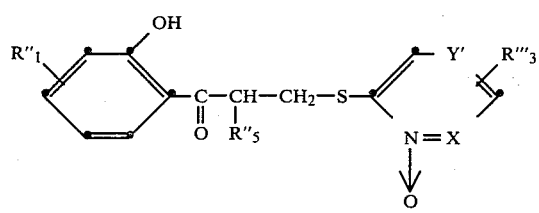 (6)

in which X and Y' are as defined under formula 5 and $R_1''$ is hydrogen, chlorine or methyl, $R_5'''$ is hydrogen, chlorine or methyl and $R_5''$ is hydrogen or a group of the formula:

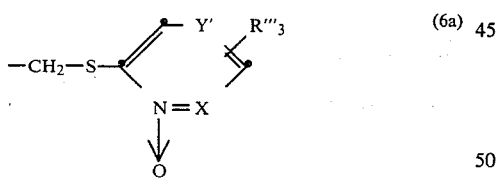 (6a)

in which X, Y' and $R_3'''$ are as defined above.

Preferred compounds of the formulae (1) to (6) are those in which X and Y or Y' are each a carbon atom.

Particularly preferred compounds are the hydroxyphenyl ketones of the formulae:

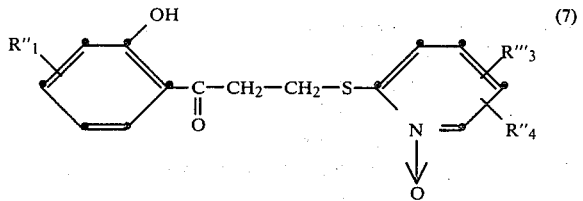 (7)

and

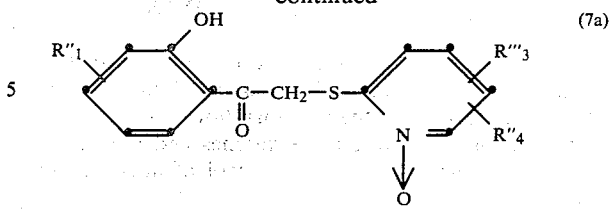 (7a)

in which $R_1''$, $R_3'''$ and $R_4''$ each independently of one another are hydrogen, chlorine or methyl.

The novel compounds of the formulae (1) to (7) can be prepared by diverse processes, which likewise are a subject of the invention.

One such process for the preparation of compounds of the formula (1) in which n=1, and thus also of the subsidiary formulae (2) to (7), comprises reacting approximately 1 mol equivalent of a Mannich base of the formula:

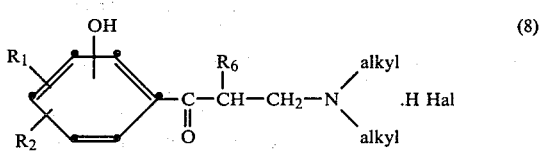 (8)

in which $R_1$ and $R_2$ are as defined under formula (1) and Hal is a halogen atom and $R_6$ is hydrogen or a group of the formula:

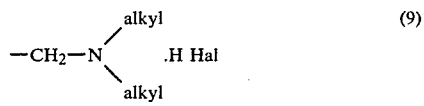 (9)

with approximately one mol equivalent (if $R_6$ is hydrogen) or with about 2 mol equivalents (if $R_6$ is not hydrogen) of a thiol of the formula:

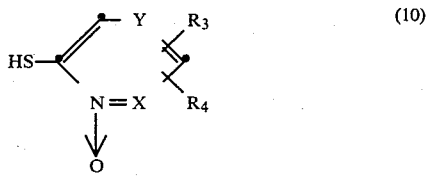 (10)

in which X, Y, $R_3$ and $R_4$ are as defined under formula (1).

In formulae (8) and (9) Hal is preferably chlorine or bromine, in particular chlorine. The alkyl groups in the Mannich base have preferably 1 to 6 and in particular 1 to 4 C atoms.

The reaction of the Mannich base of the formula (8) with the thiol of the formula (10) is preferably carried out in an inert solvent, in particular in an alcoholic or aqueous/alcoholic medium. Alcohols used are in particular lower aliphatic alcohols having 1 to 6 and preferably 1 to 4 C atoms. The reaction is advantageously carried out at elevated temperature, preferably at the boiling point of the solvent or solvent mixture used. The reaction can be carried out analogously to the procedure described by A. S. Angeloni et al. in J. Chem. Soc. [C] 1968, 2295.

The Mannich bases of the formula (8) in which $R_6$ is hydrogen can be obtained in accordance with the equation:

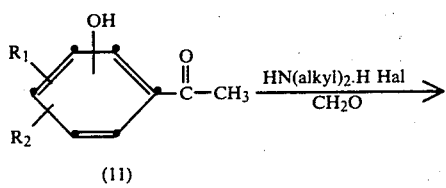

(11)

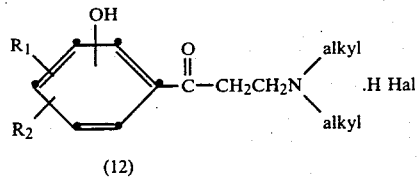

(12)

and in particular in accordance with the methods described by J. A. Gautier et al., C.R. Acad. Sci. 258, 3731 (1964) and by E. O. Taylor and W. L. Nobles, J.Am. Pharm. Assoc. Sci. Ed. 49, 317 (1960).

The compounds of the formula 11 are known or can be prepared by known methods, for example from the corresponding penols and acetyl chloride by a Friedel-Crafts reaction, if necessary followed by separation of a o-/p-isomer mixture which is obtained under certain circumstances.

The compounds of the formula (8) in which $R_6$ is a group of the formula (9) can be obtained analogously to the above reaction equation from compounds of the formula (12) by a Mannich reaction with an amine of the formula $HN(alkyl)_2 \cdot H\ Hal$ and formaldehyde.

The thiols of the formula (10) are known, specifically from the following literature sources:

| Thiol | Literature source |
|---|---|
| (13) HS—[pyrimidine-N-oxide with $R_3$, $R_4$] | U.S. Pat. Specification 2,754,826  U.S. Pat. Specification 4,048,181 |
| (14) HS—[pyrimidine-N-oxide with $R_4$, $R_4$] | U.S. Pat. Specification 4,041,033 |
| (15) HS—[triazine-N-oxide with $R_3$, $R_4$] | U.S. Pat. Specification 4,101,546 |
| (16) HS—[quinoline-N-oxide] | U.S. Pat. Specification 3,961,054 |
| (17) HS—[quinazoline-N-oxide] | U.S. Pat. Specification 3,971,725 |
| (18) HS—[quinoxaline di-N-oxide] | From 2-chloroquinoxaline di-N—oxide (German Offenlegungsschrift 2,312,730) and NaHS by known methods (U.S. Pat. Specification 4,080,329) | or can be obtained easily analogously to the methods indicated in the said literature sources.

Further processes for the preparation of compounds of the formula (1) in which $R_5$ is hydrogen and n is 0 can be represented by the following two reaction equations:

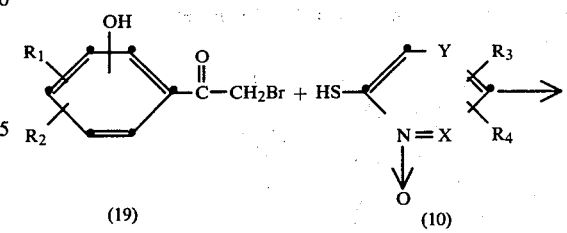

(19)    (10)

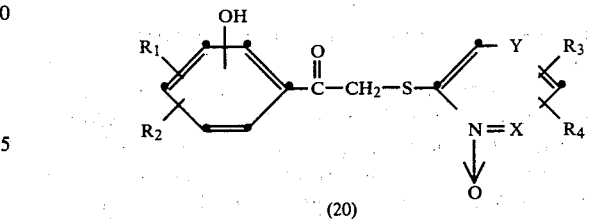

(20)

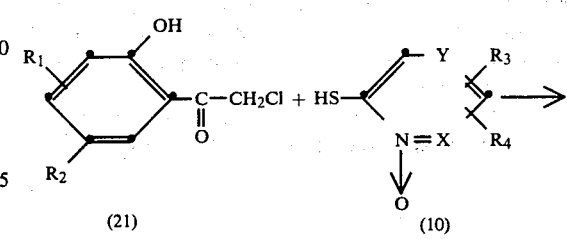

(21)    (10)

(22)

The above two reactions can be carried out in water, in alcohols or in dimethylformamide, dimethylsulfoxide, acetonitrile or similar solvents, preferably in the presence of a strong base, in particular of an alkali metal alcoholate or alkali metal hydroxide, for example at room temperature. In this context cf. U.S. Pat. No. 3,772,307.

The compounds of the formula (19) can be obtained by the method of L. C. Kinz and Ch. K. Ostrum, J. Org. Chem. Soc. 29, 3459 (1964), and the compounds of the formula (21) can be obtained by the method of N. M.

Cullinane and B. F. R. Edwards, J. Appl. Chem. 9, 133 (1959).

A further process for the preparation of compounds of the formula (1) in which $R_5$ is hydrogen and the hydroxyl group is in the 3-position only when n is 0, and thus also of compounds of the corresponding subsidiary formulae, comprises reacting a compound of the formula:

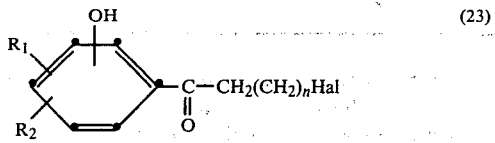

in which $R_1$, $R_2$ and n are as defined under formula (1) and Hal is chlorine or bromine, Hal being only bromine if the hydroxyl group is in the 3-position (only possible when n=0), with a thiol of the formula:

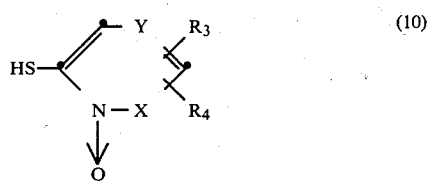

in which X, Y, $R_3$ and $R_4$ are as defined under formula (1).

The reaction is advantageously carried out in an inert solvent, in particular in water, alcohols, dimethylsulfoxide, dimethylformamide, acetonitrile or similar solvents or in mixtures of such solvents, preferably in the presence of a strong base, in particular of alkali metal alcoholates or alkali metal hydroxides. The reaction is preferably carried out at about room temperature if n=0, and in all other cases is preferably carried out at between 60° and 100° C.

The compounds of the formula (23) can be obtained, for example, in accordance with the following reaction equation:

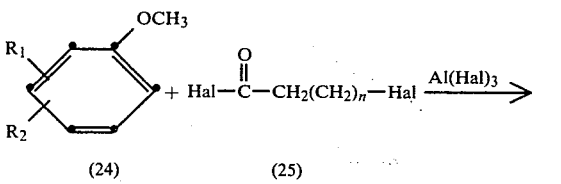

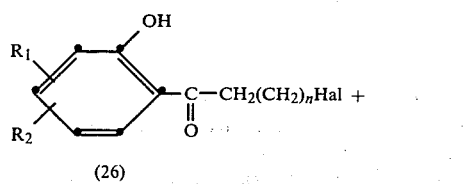

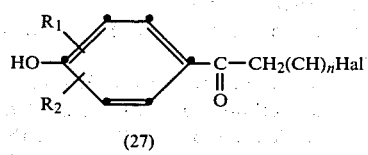

In the above formulae Hal is chlorine or bromine. The compounds of the formulae (24) and (25) are known.

The reaction (24)+(25) is carried out in the presence of a Friedel-Crafts catalyst, preferably of $AlCl_3$ or $AlBr_3$. The reaction can be carried out without a solvent, or a solvent customary in Friedel-Crafts reactions is used, for example carbon disulfide, carbon tetrachloride, chloroform, methylene chloride, nitromethane, nitroethane, nitrobenzene, diethyl ether, petroleum ether or dimethylsulfoxide.

In the case of para-substituted anisoles of the formula (24) only one compound (26) is obtained, and in the case of 2,6-disubstituted anisoles (24) or an unsubstituted ansile only one compound (27) is obtained. In all other cases mixtures of compounds of the formulae (26) and (27) are obtained. These can be separated by conventional methods.

The compounds of the formula (23) can also be obtained by acylation of the corresponding phenols with ω-halogenoalkanoic acid halides, ω-halogenoalkanoic acid anhydrides, ω-halogenoalkanoic acids and ω-halogenoalkanoic acid esters in the presence of a condensing agent, for example $AlCl_3$, $AlBr_3$, $ZnCl_2$, $BF_3$ or polyphosphoric acid (in this context cf. G. A. Olah, Friedel-Crafts and Related Reactions, Volume I (1963), 91).

Because of their broad antimicrobial spectrum of action, which in particular extends both to Gram-positive and Gram-negative bacteria as well as fungi and yeasts, the compounds, according to the invention, of the formula (1) are of particular importance. From the standpoint of application technology, the fact that these compounds are colourless and odourless and also of low toxicity is a particular advantage.

The invention therefore also relates to a method for the control of micro-organisms on or in organic or inorganic substrates and for protecting these substrates against micro-organisms, which method comprises incorporating in, or applying to the surface of, the said substrates at least one compound of the formula (1).

The present invention also relates to antimicrobial compositions which are characterised by a specific content of one or more of the compounds defined under formula (1). Depending on the use of the method, these compositions can contain diverse assistants and solvents. The compounds according to the invention are readily soluble in organic solvents and in propellant gases for aerosols. The compositions according to the invention can therefore contain such solvents and propellant gases if it is desired to spray or apply them to surfaces. Of course, the compounds according to the invention can also be dispersed or emulsified in water. Further assistants which the compositions according to the invention can contain are listed in the survey provided further below of the fields of application for the compounds of the formula (1). At this point mention may be made of the following assistants of this type: anionic wetting agents, such as soaps and benzenesulfonates, cationic wetting agents, such as alkyl-argyl sulfate, non-ionic wetting agents, such as polyglycol ethers and higher fatty alcohols, chelating agents, such as sodium hexametaphosphate, aromatic substances, foaming agents, emulsifiers, plasticisers, softeners, light stabilisers, finishing agents, fillers, such as silicates, carbonates and/or starch derivatives, and pharmaceutical and/or cosmetic formulations.

The compounds according to the invention can, of course, also be formulated with a solid carrier to give, for example, pulverulent compositions.

Use of the compounds of the formula (1) and of the compositions containing them is possible on a very broad basis, in particular for protection of organic substrates against attack by harmful and pathogenic micro-organisms. Accordingly, the antimicrobial agents mentioned are suitable, inter alia, as preservatives and disinfectants for industrial products of all types, and also for deodorising.

A preferred field of application of the compounds of the formula (1) is the preservation of technical formulations. Examples of such formulations which may be listed are: glues, binders, paints, textile assistants and finishing agents, colour pastes and printing pastes, lacquers and similar preparations based on organic and inorganic dyes and pigments, including those which contain added casein or other organic compounds. Wall and ceiling paints, for example those which contain an albuminous colour binder, are also protected by the addition of compounds according to the invention against attack by micro-organisms.

Further fields of use are: preservation of formulations containing agricultural chemicals, of water-based adhesives, for example of wallpaper adhesives, against attack by micro-organisms, and prevention and control of bacterial and fungus infections in animal oils, fats and oily emulsions, such as cutting oils and boring oils. If coating compositions, lacquers and paints are preserved with the aid of compounds according to the invention, the film coatings produced therefrom are also protected against attack by micro-organisms. It is also possible to protect plasticisers, permanent sizes (for example based on polyvinyl alcohol) or starch sizes. Plastic compositions of all types, for example derived from polyamides, polycarbonates, polyesters, polyvinyl chloride, polypropionate or polyvinyl alcohol, are also advantageously protected by compounds according to the invention against attack by bacteria and fungi. When using plasticisers, it is advantageous to add the antimicrobial additive as a solution or dispersion in the plasticiser to the plastic. It is expedient to ensure as uniform as distribution as possible in the plastic. The resulting plastics can be used for commodities of all kinds in which an action against germs of the most diverse kinds, for example bacteria and fungi, is desired, thus, for example, for footmats, bathroom curtains, seating, grip channel gratings in swimming pools, wall hangings and the like. By incorporation in corresponding wax compositions and floor polishes, floor and furniture care products are obtained which have a disinfectant action.

To achieve the desired effect, the active compound or compounds of the formula (1) is or are mixed into the said formulations and distributed therein as homogeneously as possible. For this purpose, the active compound can be employed on its own in the appropriate amount or can be used as a solution or dispersion in a solvent or dispersant, which may additionally contain further assistants. The amount of active compound should be not less than 10 ppm, based on the material to be protected, and for practical reasons suitable amounts are about 100 to 10,000 and preferably 200 to 5,000 ppm.

The compounds, according to the invention, of the formula (1) can also be used for protecting a very wide variety of surfaces from attack by bacteria and fungi. In this connection particular mention may be made of the treatment of wood (as raw material), manufactured articles made from wood, wood shavings, sawdust, leather, hides and pelts. However, disinfection and protection of containers in which, for example, technical formulations are stored and of floors and walls of animal sheds, slaughterhouses and the like is also possible with the aid of the method according to the invention. Depending on the shape of the object to be protected, the said articles or surfaces are sprayed (for example with the aid of a spray), or coated or impregnated (for example wood and leather) with an aqueous or organic solution or dispersion containing the active compound.

Examples of suitable organic solvents are water-immiscible solvents, in particular petroleum fractions, but also water-miscible solvents, such as lower alcohols (for example ethanol and methanol), ethylene glycol monomethyl ether or ethylene glycol monoethyl ether.

Preferably, the composition according to the invention is applied in an amount such that the particular article contains about 0.01 to 10 g/m$^2$ of the active compound after the treatment. In the treatment of wood it is possible, in particular, to prevent or delay the discoloration and rotting caused by various fungi during storage.

The compounds of the formula (1) and the method according to the invention can also be employed in the pulp and paper industry. In this case, in particular the formation of slime caused by micro-organisms in the machinery used for papermaking is prevented by this means. For this purpose, the corresponding active compound is added either to the paper pulp or to the recirculating water system in the paper factory. The method according to the invention can also be used in an analogous form in other industrial plants where contamination by micro-organisms is to be expected. The amount of active compound should as a rule be not less than 1 ppm, and in practice about 10 to 10,000, preferably 20 to 5,000, ppm.

Detergents and cleansing agents having an excellent antibacterial or antimycotic action are obtained by combining the compounds according to the invention with surface-active substances, especially detergent substances.

The cleansing agents can be in any desired form, for example in liquid, pasty, solid, flake or granular form. The active compounds can be incorporated either into anionic compounds, such as soaps and other carboxylates (for example alkali metal salts of higher fatty acids), derivatives of oxyacids of sulfur (for example the sodium salt of dodecylbenzenesulfonic acid or water-soluble salts of sulfuric acid monoesters of higher-molecular alcohols or of their polyglycol ethers, for example soluble salts of dodecyl alcohol sulfate or of dodecyl alcohol polyglycol ether sulfate), derivatives of oxyacids of phosphorus (for example phosphates) or derivatives with acid (electrophilic) nitrogen in the hydrophilic group (for example disulfine salts) or into cationic surfactants, such as amines and their salts (for example lauryldiethylenetriamine), onium compounds, amine oxides or non-ionic surfactants, such as polyhydroxy compounds, surfactants based on a monosaccharide or polysaccharide, higher-molecular acetylene glycols, polyglycol ethers (for example polyglycol ethers of higher fatty alcohols or polyglycol ethers of higher-molecular alkylated phenols), or in mixtures of surfactants of different types. The antimicrobial activity of the active compounds is retained in full in these compositions. The content of active compound in the cleansing agent, based on the weight of this agent, is in general 0.01 to 20% and in most cases 0.01 to 3%. Aqueous preparations of such cleansing agents, which contain the active compounds, can be used, for example, for providing textile materials with an antimicrobial finish; they are also suitable as antimicrobial cleansing agents in the foodstuffs and drinks industries, for example in breweries, dairies, cheese-dairies, animal sheds and slaughterhouses.

Furthermore, the compounds according to the invention can also be incorporated into cosmetic preparations, for example soaps of very diverse types, ethereal oils, bath salts, brilliantines, ointments, facial tonics, hair dyes, hair oils, hair tonics, skin creams, skin oils, eau de Cologne, perfumes, powders, make-up, depilatories, anti-sunburn preparations, dental care products and the like, an additional antimicrobial and deodorising action being imparted to these preparations in this way. In general an active compound content of 0.001 to 5% and preferably of 0.01 to 3%, based on the total weight of the preparation, suffices for this purpose. The compounds according to the invention are particularly suitable as active compounds in disinfectants for hands.

The compounds according to the invention can also be used for disinfecting laundry, for example doctors' clothing and hospital laundry, and providing it with a finish, and for disinfecting a wide variety of articles, for example in the medical field. Diverse surfaces, for example of metal or plastics, coats of paint and others, can be disinfected by compositions according to the invention. Such surfaces are floor coverings, carpeting, walls and fittings.

The compounds according to the invention are also of importance for removing germs from goods for washing and for protecting the washed goods against attack by micro-organisms.

Goods for washing which can be de-germed with compositions according to the invention are, in particular, organic fibre material, specifically organic fibre material of natural origin, such as cellulose-containing fibre material, for example cotton, or polypeptide-containing fibre material, for example wool or silk, or fibre material of synthetic origin, such as that based on polyamide, polyacrylonitrile or polyester, or mixtures of the abovementioned fibres.

The compounds according to the invention impart to the washed goods treated therewith substantial sterility against forms of *staphylococci, coli* and *pseudomonas*. A particular advantage of the compositions according to the invention is that the removal of germs, including *pseudomonades,* can be carried out at low temperatures and under mild conditions, and it is not necessary to add further substances which are harmful or pollute the environment.

The compounds according to the invention are also very effective against the bacterial flora which give rise to perspiration odour and for this reason, and because of their low toxicity, are suitable as deodorising agents for laundry or for cosmetics.

Furthermore, the compounds according to the invention are used for providing fibres and textiles with a preservative and disinfectant finish, the active compounds being applied to natural and synthetic fibres, preferably natural fibres, for example of cellulose, on which they exert a lasting action against harmful (including pathogenic) micro-organisms, for example fungi and bacteria. The compounds can be added before, simultaneously with or after a treatment of these textiles with other substances, for example colour or printing pastes, flame retardants, fabric softeners and other finishing agents and the like.

Textiles treated in this way are protected against rotting induced by micro-organisms.

The formulations in which the active compounds according to the invention are applied can correspond to the conventional formulations. The compositions used for finishing and protecting textiles should contain the compounds according to the invention in a finely divided form. In particular solutions, dispersions and emulsions of the active compounds are therefore used. Aqueous dispersions can be obtained, for example, from pastes or concentrates and can be applied as liquids or as an aerosol.

The aqueous solutions or dispersions accordingly advantageously contain surfactants, for example anionic compounds, such as soaps and other carboxylates (for example alkali metal salts of higher fatty acids), derivatives of oxyacids of sulfur (for example the sodium salt of dodecylbenzensulfonic acid or water-soluble salts of sulfuric acid monoesters of higher-molecular alcohols or of their polyglycol ethers, for example soluble salts of dodecyl alcohol sulfate or of dodecyl alcohol polyglycol ether sulfate), derivatives of oxyacids of phosphorus (for example phosphates) or derivatives with acid (electrophilic) nitrogen in the hydrophilic group (for example disulfine salts), cationic surfactants, such as amines and their salts (for example lauryl-diethylenetriamine), onium compounds, amine oxides or non-ionic surfactants, such as polyhydroxy compounds, surfactants based on a monosaccharide or polysaccharide, higher-molecular acetylene glycols or polyglycol ethers (for example polyglycol ethers of higher fatty alcohols or polyglycol ethers of higher-molecular alkylated phenols). In addition, the liquor can also contain conventional assistants, such as water-soluble perborates, polyphosphates, carbonates, silicates, fluorescent brighteners, plasticisers, salts which have an acid reaction, such as ammonium silicofluoride or zinc silicofluoride, or certain organic acids, such as oxalic acid, and also finishing agents, for example those based on synthetic resin or starch.

The textile materials can, for example, be impregnated with the active compounds by means of hot or cold dyeing, bleaching, chroming or after-treatment baths, and various textile finishing processes can be used for this, for example the pad or exhaust method.

The treatment is advantageously carried out at temperatures of 10° to 100° C., for example at 10° to 70° C., preferably at about room temperature.

Because of the good solubility in organic solvents, the compounds of the formula (1) are also very suitable for application from non-aqueous media. The materials to be finished and protected can in this case simply be impregnated with the solutions.

Examples of suitable organic solvents are trichloroethylene, methylene chloride, hydrocarbons, propylene glycol, methoxyethanol, ethoxyethanol and dimethylformamide, and dispersing agents (for example emulsifiers, such as sulfated castor oil, fatty alcohol sulfates and the like) and/or other assistants can also be added to the solvents.

Depending on the intended use, the content of active compounds according to the invention can be between 0.01 and 50 g, preferably between 0.1 and 30 g of active substance per liter of treatment liquor.

The active compounds can be used on their own or together with other known antimicrobial agents for the protection of textiles.

The textiles which are finished and protected are in the main fibres of natural origin, such as cellulose-containing fibres, for example cotton, or polypeptide-containing fibres, for example wool or silk, but also fibres of synthetic origin, such as those based on polyamide, polyacrylonitrile or polyester, or mixtures of these fibres.

The amount of active compound applied to the textile materials is preferably at least 100 ppm, based on the material.

In most cases, the textiles are adequately protected against attack by fungi and bacteria by an amount of 100 to 10,000, preferably 300 to 5,000, ppm of active compound, based on the weight of the textile materials.

For the purposes of disinfection and preservation, the compounds of the formula (1) can also be used in combination with known antimicrobial agents. Antimicrobial agents which can be employed in this way in combination with the compounds according to the invention are, for example, those of the following categories: phenol derivatives, such as 3,5-dichlorophenol, 2,5-dichlorophenol, 3,5-dibromophenol, 2,5-dibromophenol, 2,5-(or 3,5-)dichloro-4-bromophenol, 3,4,5-trichlorophenol, 3,4,5-tribromophenol, phenylphenol, 4-chloro-2-phenylphenol, 4-chloro-2-benzylphenol, dichlorophene and hexachlorophene; aldehydes, such as formaldehyde, glutaraldehyde and salicylaldehyde; alcohols, such as phenoxyethanol; antimicrobially active carboxylic acids and their derivatives; metal-organic compounds, such as tributyl-tin compounds; iodine compounds, such as iodophores and iodonium compounds; quaternary ammonium compounds, such as benzyldimethyldodecylammonium chloride, dimethyldidecylammonium chloride and benzyl-di-(2-hydroxyethyl)-dodecylammonium chloride; sulfonium and phosphonium compounds; mercapto compounds and their alkali metal salts, alkaline earth metal salts and heavy metal salts, such as 2-mercaptopyridine N-oxide and its Na salt and Zn salt, 3-mercaptopyridazine 2-oxide, 2-mercapto-quinoxaline 1-oxide and 2-mercapto-quinoxaline di-N-oxide, and also the symmetrical disulfides of the said mercapto compounds; ureas, such as tribromocarbanilide or trichlorocarbanilide and dichlorotrifluoromethyl-diphenylurea; tribromosalicylanilide; 2-bromo-2-nitro-1,3-dihydroxypropane; dichlorobenzoxazolone; chlorohexidine; and isothiazolone and benzoisothiazolone derivatives.

The compounds, according to the invention, of the formulae (1) to (7a) can also be used successfully in plant protection. They can therefore be present as the active substances in plant protection agents. The compounds according to the invention display an action, in particular, against fungi which damage plants, for example against Puccinia species, *Botrytis zinerea* and *Venturia inaequalis*.

The following examples serve to further illustrate the invention without, however, restricting it thereto. In the examples and also in the other part of the description and in the patent claims, parts and percentages are by weight unless indicated otherwise.

EXAMPLE 1

6.4 g of bis-α,α-(dimethylaminomethylene)-2-hydroxyacetophenone dihydrochloride and 5.1 g of 2-mercaptopyridine 1-oxide are dissolved in 20 ml of anhydrous ethanol and the solution is refluxed for 15 hours. The cooled, clear solution is concentrated to half its volume in a rotary evaporator rand is then left to stand for one day at 5° C. The crystals which have separated out are filtered off and recrystallised from toluene. 4.6 g of bis-α,α-(pyridyl-1-oxide-2-thiomethylene)-2′-hydroxyacetophenone of the formula:

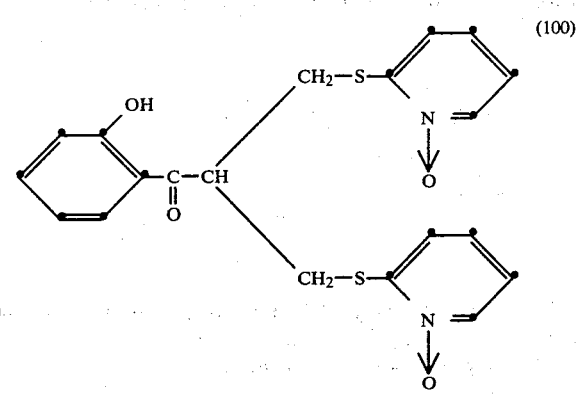

are thus obtained in the form of slightly brownish crystals with a melting point of 126°–127° C.

The compounds of the formulae:

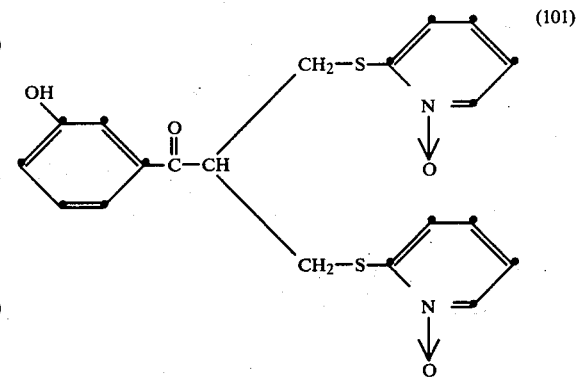

and

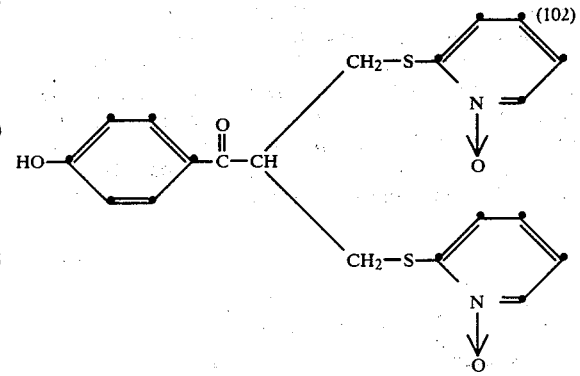

are obtained in an analogous manner using the corresponding Mannich bases of 3- and 4-hydroxyacetophenone respectively.

The Mannich bases required as starting compounds are obtained as follows:

45.9 g of β-dimethylamino-2-hydroxy-propiophenone hydrochloride, 33 g of dimethylamine hydrochloride and 10 g of paraformaldehyde are stirred into a mixture of 70 ml of ethanol and 0.5 ml of concentrated hydrochloric acid. After stirring under reflux for 1½ days, the solution is cooled to room temperature, 300 ml of acetone are added and the mixture is left to stand for 15 hours at 5° C. The substance which has precipitated is filtered off with suction and dried in a drying cabinet at 80° C. 33.9 g of bis-α,α-(dimethylaminomethylene)-2-hydroxyacetophenone dihydrochloride of the formula:

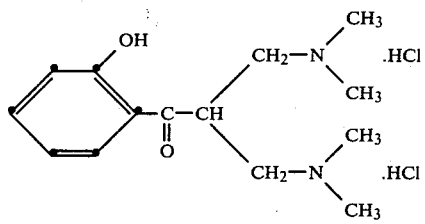
(103)

are obtained in this way in the form of colourless crystals with a melting point of 220°–230° C.

The Mannich bases of the formulae:

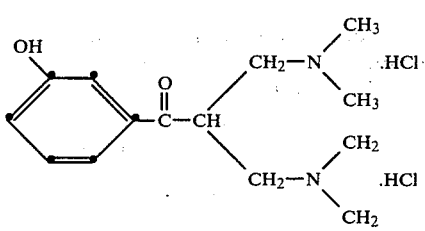
(104)

and

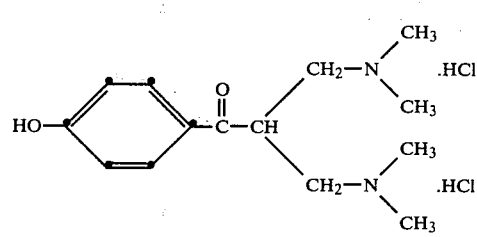
(105)

are obtained in an analogous manner using β-dimethylamino-3-hydroxy-propiophenone and β-dimethylamino-4-hydroxypropiophenone respectively.

The β-dimethylamino-hydroxy-propiophenones required for the preparation of the Mannich bases of the type of the formulae (103) to (105) are prepared by known methods, for example by the method of J. A. Gautier et al., C. R. Acad. Sci. 258 (1964), 3731; for example the compounds of the formula:

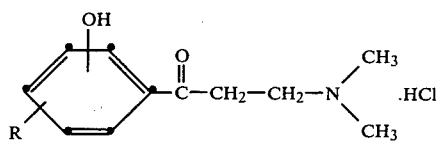
(106)

listed in Table 1 are prepared in this way.

TABLE 1

| Compound No. | Position of OH | R | Melting Point (°C.) |
|---|---|---|---|
| 107 | 2-OH | H | 176–178 |
| 108 | 3-OH | H | 181–182 |
| 109 | 4-OH | H | 196–198 |
| 110 | 2-OH | 5-Cl | 187–190 |

TABLE 1-continued

| Compound No. | Position of OH | R | Melting Point (°C.) |
|---|---|---|---|
| 111 | 2-OH | 4-OCH₃ | 168–169 |

EXAMPLE 2

45.9 g of β-dimethylamino-2-hydroxypropiophenone hydrochloride and 25.4 g of 2-mercaptopyridine 1-oxide are dissolved in 200 ml of methanol and the solution is refluxed for 15 hours. The clear solution is cooled to 5° C. and left to stand for 15 hours at this temperature. The crystals (49 g) which have separated out are filtered off with suction and have a melting point of 159°–163° C. After recrystallisation from chloroform, 43 g of β-(pyridyl-1-oxide-2-thio)-2'-hydroxypropiophenone of the formula:

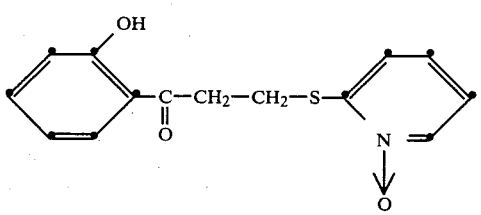
(200)

are obtained in the form of slightly brownish crystals with a melting point of 162°–164° C.

The compounds of the formula:

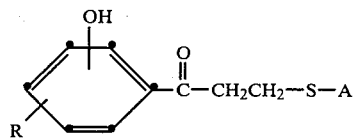
(201)

listed in Table 2 are obtained in an analogous manner using the suitable starting materials:

TABLE 2

| Compound No. | Position of OH | R | A | Melting point (°C.) |
|---|---|---|---|---|
| 202 | 3-OH | H | 2-pyridyl-1-oxide | 187–191 |
| 203 | 4-OH | H | 2-pyridyl-1-oxide | 234–235 |
| 204 | 2-OH | 5-Cl | 2-pyridyl-1-oxide | 177–179 |
| 205 | 2-OH | H | 3-pyridazinyl-2-oxide | 109–112 |
| 206 | 2-OH | H | 3-pyridazinyl-6-chloro-2-oxide | 174–177 |
| 207 | 2-OH | H | 2-pyrazinyl-1-oxide | |
| 208 | 2-OH | H | 2-quinolyl-1-oxide | |
| 209 | 2-OH | H | 2-quinoxalinyl-1-oxide | |
| 210 | 2-OH | H | 2-quinoxalinyl-1,4-dioxide | |
| 211 | 2-OH | 4-OCH₃ | 2-pyridyl-1-oxide | 145–147 |

EXAMPLE 3

12.7 g of α-bromo-2-hydroxyacetophenone, 6.35 g of 2-mercaptopyridine 1-oxide and 2.7 g of sodium methylate are dissolved in 100 ml of anhydrous ethanol and the solution is stirred for 18 hours at room temperature; a viscous suspension forms. This is left to stand for 15 hours at 5° C. and the insoluble material is then filtered off. The residue is recrystallised from ethanol, whereupon 9.5 g of α-(pyridyl-1-oxide-2-thio)-2'-hydroxyacetophenone of the formula:

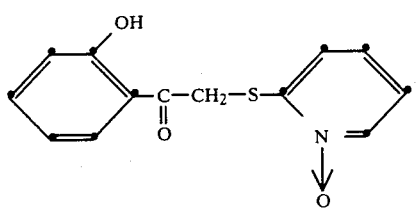 (300)

are obtained in the form of slightly brownish crystals with a melting point of 151°–153° C.

The compounds of the formula:

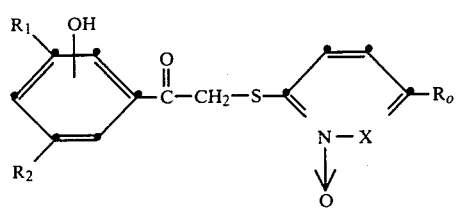

listed in Table 3 are obtained in an analogous manner using the corresponding starting materials.

TABLE 3

| Compound No. | Position of OH | $R_1$ | $R_2$ | X | Melting point (°C.) | $R_o$ |
|---|---|---|---|---|---|---|
| 302 | 2-OH | H | Cl | C | 195–197 | H |
| 303 | 2-OH | H | $CH_3$ | C | 180–181 | H |
| 304 | 2-OH | Cl | Cl | C | 177–180 | H |
| 305 | 3-OH | H | H | C | 189 (decomposition) | H |
| 306 | 4-OH | H | H | C | 195 (decomposition) | H |
| 307 | 2-OH | H | H | N | 158–164 | H |
| 307a | 2-OH | H | H | N | 207–209 | Cl |

The α-halogenohydroxyacetophenones required as starting materials in the above example are prepared by known methods, for example by the method of L. C. King and G. K. Ostrum, J. Org. Chem. 29, 3459 (1964) (=method a) or by the method of N. M. Cullinane and B. F. R. Edwards, J. Appl. Chem. 9, 133 (1959) (=method b); for example the compounds of the formula:

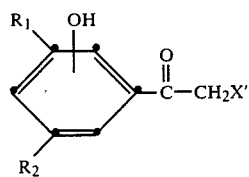

listed in Table 4 below are prepared in this way.

TABLE 4

| Compound No. | Position of OH | $R_1$ | $R_2$ | X' | Method | Melting point (°C.) |
|---|---|---|---|---|---|---|
| 308 | 2-OH | H | H | Br | a | 41–43 |
| 309 | 2-OH | Cl | Cl | Cl | b | 132–134 |
| 310 | 2-OH | H | $CH_3$ | Cl | b | 62–63 |
| 311 | 2-OH | H | Cl | Cl | b | 107–110 |
| 312 | 3-OH | H | H | Br | a | dark resin |
| 313 | 4-OH | H | H | Br | a | dark resin |

EXAMPLE 4

20.9 g of δ-chloro-2-hydroxy-5-chlorovalerophenone, 10.2 g of 2-mercaptopyridine 1-oxide and 4.3 g of sodium methylate are dissolved in 150 ml of anhydrous ethanol and the solution is refluxed for 15 hours. The solution, which has been cooled to room temperature, is discharged into 500 ml of water and the resulting mixture is stirred for 1 hour. The solid is filtered off with suction and dried in a drying cabinet at 60° C. 26.2 g of a brownish substance with a melting point of 192°–199° C. are obtained. This substance is stirred in hot chloroform, the mixture is left to stand for 15 hours at 5° C. and the insoluble solid is then filtered off and dried. 22 g of δ-(pyridyl-1-oxide-2-thio)-2'-hydroxy-5-chlorovalerophenone of the formula:

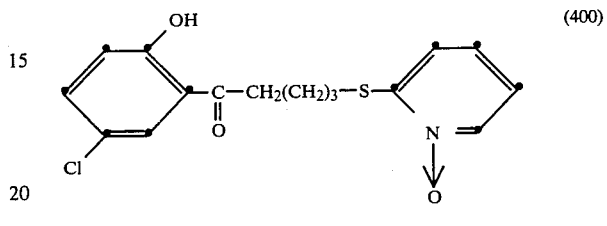 (400)

are thus obtained in the form of a brownish substance with a melting point of 205°–207° C.

The compounds of the formula:

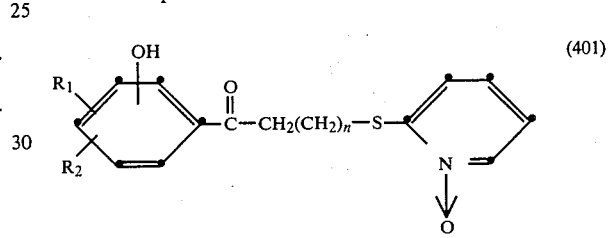 (401)

listed in Table 5 are obtained in an analogous manner using the corresponding ω-chloro-hydroxyacylphenones.

TABLE 5

| Compound No. | Position of OH | $R_1$ | $R_2$ | n | Melting point (°C.) |
|---|---|---|---|---|---|
| 402 | 4-OH | H | H | 2 | 194–197 |
| 403 | 2-OH | H | 5-Cl | 2 | 130–132 |
| 404 | 2-OH | 4-Cl | 5-Cl | 1 | 207–208 |
| 405 | 2-OH | H | 5-$CH_3$ | 2 | 108–110 |
| 406 | 2-OH | H | 5-F | 2 | 186–189 |
| 407 | 2-OH | H | 5-F | 3 | |
| 408 | 2-OH | H | H | 2 | |
| 409 | 2-OH | 4-Cl | 5-Cl | 2 | |
| 410 | 2-OH | H | H | 3 | |
| 411 | 4-OH | H | H | 3 | |
| 412 | 4-OH | 2-Cl | 3-Cl | 1 | 213–215 |

The ω-chloro-2-hydroxyacylphenones required as starting materials in the above example are obtained as follows:

42.8 g of 4-chloroanisole are dissolved in 30 ml of nitroethane. 53.4 g of $AlCl_3$ are introduced in portions, at not more than 35° C., with ice-cooling. 42.3 g of γ-chlorobutyric acid chloride are added dropwise at a temperature of 10°–15° C. and the mixture is then stirred at room temperature for 18 hours. The resulting suspension is discharged into water and the mixture is extracted with chloroform. The chloroform phase is washed until neutral, dried and evaporated, whereupon 69.6 g of a brown oil remain. After 2 days at 5° C. the oil partially crystallises. The resulting crystal slurry is ground on a clay plate. 53.5 g of γ-chloro-2-hydroxy-5-chlorobutyrophenone of the formula:

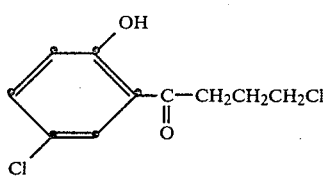

are thus obtained in the form of colourless crystals with a melting point of 41°–42° C.

The ω-chloro-hydroxyacylphenones of the formula:

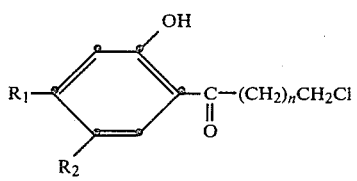

listed in Table 6 are obtained in an analogous manner.

TABLE 6

| Compound No. | $R_1$ | $R_2$ | n | Melting point (°C.) |
|---|---|---|---|---|
| 414 | H | CH$_3$ | 2 | 39–41 |
| 415 | H | F | 2 | 62–66 |
| 416 | H | F | 3 | |
| 417 | Cl | Cl | 1 | 117–119 |
| 418 | H | Cl | 3 | 70–71 |
| 419 | H | H | 2 | |

The ω-chloro-4-hydroxyacylphenones which are likewise required as starting materials are obtained by the following method:

32.4 g of anisole are dissolved in 30 ml of chlorobenzene. 53.6 g of AlCl$_3$ are introduced in portions, at not more than 35° C., with ice-cooling. 42.3 g of γ-chlorobutyric acid chloride are added dropwise at a temperature of 15°–35° C. and the mixture is then slowly warmed to 100° C. After stirring for three hours at 100° C., the mixture is cooled to room temperature and discharged into water and the mixture is then extracted with ether. Evaporation of the ether phase, after this has been washed until neutral and dried, yields a reddish solid. This is recrystallised from hexane/ethanol using active charcoal. 45 g of γ-chloro-4-hydroxybutyrophenone of the formula:

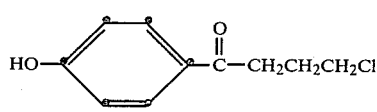

are then obtained in the form of colourless crystals with a melting point of 108°–111° C.

The compound of the formula:

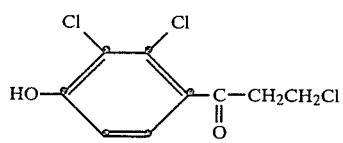

which has a melting point of 92°–95° C. is obtained in an analogous manner.

EXAMPLE 5

Test of the bactericidal and fungicidal activity of the active compounds of the formulae (100)–(102), (200), (202)–(211), (300), (302)–(307), (400) and (402)–(412) in the suspension test:

In each case a phosphate buffer medium (pH 5, 7 or 8) containing 1,000, 100, 10, 1 or 0.1 ppm of the active compound to be tested is inoculated with one test strain (bacteria: O/n cultures; fungi: spore suspension, 14-day cultures) (final concentration 10$^6$ germs/ml). After an incubation period of 18 hours at 20° C. on a magnetic stirrer, the mixtures are tested to determine at which concentration the germs have been killed. All of the compounds tested exhibit an excellent germicidal action in this test.

The test germs used are:
*Staph. aureus:* ATCC 6538;
*E. coli:* ATCC 11229;
*Ps. aeruginosa:* ATCC 15442;
*Aspergillus niger:* ATCC 6275.
Medium: Sörensen phosphate buffer (1/15 molar) with 2% of brain heart infusion broth.

EXAMPLE 6

Test of the bacteriostatic and fungistatic activity of the active compounds of the formulae (100)–(102), (200), (202)–(211), (300), (302)–(307), (400) and (402)–(412) using the agar incorporation test:

A 5% stock solution of each active compound in ®methylcellosolve (methylglycol) is prepared. A dilution series is prepared from this stock solution, so that the concentrations in the individual solutions differ by a power of ten from one solution to the next. 0.3 ml amounts of the solutions thus obtained are put into sterile Petri dishes, and each solution is mixed with 15 ml of hot, liquid nutrient medium (nutrient agar). The nutrient medium then contains 1,000, 100, 10, 1 or 0.1 ppm of active substance.

After the plates have congealed, the particular germ suspensions (the germs used are the same as in Example 5) are dripped thereon using a Pasteur pipette or the inoculation device. The incubation time for bacteria is 24 hours at 37° C. and for Aspergillus niger is 3 days at 28° C. The plates are then assessed to determine up to which concentration of active substance the germs have grown. The compounds tested exhibit a good bacteriostatic and fungistatic action against the germs tested.

EXAMPLE 7

The compounds of the formulae (100)–(102), (200), (202)–(211), (300), (302)–(307), (400) and (402)–(412) are incorporated, together with soap, into a nutrient medium and the activity is determined using the agar incorporation test. The following test germs are used:
*Staph. aureus:* ATCC 6538;
*Strept. faecalis:* ATCC 10541;
*Corynebacterium minutissimum:* NCTC 10288;
*Escherichia coli:* NCTC 8196;
*Salmonella typhimurium:* NCTC 5710;
*Pseudomonas aeruginosa:* NCTC 8060;
*Candida albicans:* ATCC 10259.
*Trich. mentagrophytes:* ATCC 9533;
nutrient medium for bacteria: tryptone glucose extract agar;
nutrient medium for fungi: mycophil agar.

A 0.5% solution is prepared from a base soap composition using sterile water.

This stock solution is added to hot, sterile, liquid agar in an amount such that the nutrient medium contains 500 ppm of soap.

The test substances are dissolved in dimethylsulfoxide to give solutions containing 500 ppm. 0.1, 0.05 and 0.01 ml amounts of active substance solution are put into sterile Petri dishes, 10 ml of nutrient medium containing 500 ppm of soap are added to each dish and the contents of each dish are mixed well. (Thus, the amount of active substance mixed in the nutrient medium is 5, 2.5 and 0.5 ppm respectively.)

After the plates have congealed, the germ suspensions are dripped on using a Pasteur pipette or the inoculation apparatus. The incubation time for bacteria is 24 hours at 37° C. and for fungi is 5 days at 28° C. An assessment is made to determine whether or not the germs have grown.

The compounds tested in this way exhibit a good activity against the micro-organisms used.

EXAMPLE 8

The compounds of the formulae (100)–(102), (200), (202)–(211), (300), (302)–(307), (400) and (402)–(412) are dissolved in a suitable formulation (ethylcellosolve/dimethylformamide). The three substrates listed below are placed in the formulation baths and then squeezed out between 2 aluminium sheets; the substrates are then air-dried. Squeezing is carried out in such a way that 1,000 ppm of active substance are present on the fabric.
1. Reinforced cotton, causticised and bleached;
   Weight per m$^2$: 121 g;
2. Polyamide, nylon staple fabric, fixed and bleached;
   Weight per m$^2$: 140 g;
3. Polyester, Dacron staple fabric, type 54, fixed and bleached;
   Weight per m$^2$: 130 g.

The substrates are then tested against the 7 test organisms listed below, using the agar diffusion test (modified AATCC test method 90, 1970).
Bacteria
   *Staphylococcus aureus:* ATCC 6538;
   *Escherichia coli:* NCTC 8196;
   *Proteus mirabilis:* NCTC 8309;
   *Pseudomonas aeruginosa;* NCTC 8060.
Fungi
   *Candida albicans:* ATCC 10259;
   *Trichophyton mentagrophytes:* ATCC;
   *Aspergillus niger:* ATCC 6275.

The test plates consist of a twin-layer agar, i.e. of a base layer of uninoculated nutrient agar and a top layer of inoculated nutrient agar.
Bacteria: nutrient agar; Fungi: mycophil agar.

The filtered germ suspension is poured onto a congealed base layer and, after the inoculated layer has congealed, discs, 20 mm in diameter, of the treated substrates are placed thereon. The bacteria and Candida plates are incubated for 24 hours at 37° C. and the fungi plates are incubated for 3 to 5 days at 28° C. After incubation, the plates are evaluated for inhibition zones. If there is no inhibition zone, the growth beneath the test sample is checked using a magnifying glass.

The abovementioned compounds tested in this way exhibit, in conjunction with the substrates used, a good action against the bacteria and fungi used.

EXAMPLE 9

Raw paper which consists of 90% of bleached sulfite cellulose and 10% of birch is impregnated in a sizing press with a 2.5% solution of, in each case, one of the compounds of the formulae (100)–(102), (200), (202)–(211), (300), (302)–(307), (400) and (402)–(412) in 2:1 methanol/water so that the increase in weight is 40%.

The dried paper contains 1% of active compound, based on its own weight.

To test the action against bacteria, discs of the impregnated paper measuring 10 mm in diameter are placed on brain heart infusion agar plates which have been inoculated beforehand with Staphylococcus aureus. The plates are then incubated for 24 hours at 37° C.

To test the action against fungi, discs 25 mm in diameter are placed on mycophil agar plates and then inoculated with Aspergillus niger. The plates are then incubated for 72 hours at 30° C.

Evaluation is made, on the one hand, of the inhibition zone (IZ in mm) occurring around the paper discs and, on the other hand, of the growth (G in %) which can be detected microscopically beneath or on the discs. The compounds tested exhibit a good action against the test germs used.

EXAMPLE 10

To prepare an antimicrobial bar soap, 2.4 g of one of the compounds of the formulae (100)–(102), (200), (202)–(211), (300), (302)–(307), (400) and (402)–(412) are added to the following mixture: 120 g of base soap in flake form, 0.12 g of the disodium salt of ethylenediaminetetraacetic acid (dihydrate) and 0.24 g of titanium dioxide.

The soap chips obtained by rolling are pulverised with a high-speed stirrer and then compressed to bars of soap.

Concentrated aqueous solutions of the antimicrobial soap are admixed to warm brain heart infusion agar so that incorporation dilution series containing 2, 10, 20, 100 and so on ppm of active compound result. The warm mixtures are poured into Petri dishes, allowed to solidify and then inoculated with Staphylococcus aureus.

After incubating for 24 hours at 37° C. the minimum inhibitory concentration is determined.

The compounds tested exhibit a good action against the test germs.

EXAMPLE 11

A solution of 1.00 g of one of the compounds of the formulae (100)–(102), (200), (202)–(211), (300), (302)–(307), (400) and (402)–(412) and 3.00 g of sodium sulforicinoleate in 47.00 g of polyethylene glycol 400 and a solution of 7.00 g of sodium dodecyl-sulfate in 39.85 g of water are prepared, the two solutions are mixed and 0.15 g of perfume is added to the mixture. A very effective hand disinfectant is obtained in this way and for application is dripped or sprayed onto the damp skin and rubbed in.

EXAMPLE 12

An emulsifiable concentrate is prepared by mixing the following constituents:
   10 parts of one of the compounds of the formulae (100)–(102), (200), (202)–(211), (300), (302)–(307), (400) and (402)–(412),
   68 parts of xylene,
   10 parts of dimethylformamide and
   12 parts of surface-active compound.

Before use, the concentrate is diluted with water to 50 to 500 times its volume. Wood, sawdust or cellulose fibres are immersed in the emulsion thus obtained and by this means they are protected against attack by bacteria and fungi.

EXAMPLE 13

An oil-soluble concentrate is prepared by mixing the following constituents:
  20 parts of one of the compounds of the formulae (100)–(102), (200), (202)–(211), (300), (302)–(307), (400) and (402)–(412),
  40 parts of ethylene glycol monoethyl ether,
  10 parts of dimethylformamide and
  30 parts of xylene.

The resulting concentrate is admixed to a paint liquor or a cutting oil in an amount such that the paint or oil contains 0.1% of active compound. Protection against attack by bacteria and fungi is achieved in this way.

EXAMPLE 14

The emulsifiable concentrate prepared according to Example 12 is diluted with water to 400 or 800 times its volume.

Rectangular test samples of birch wood with a side length of 5 cm and a thickness of 5 mm are immersed in the emulsion for 2 minutes and dried for 24 hours at room temperature. The samples are then laid on the surface of agar plates. Spore suspensions of Aspergillus niger are sprayed onto the agar plates and the samples. The fungi are incubated for 2 weeks at an atmospheric humidity of 95% and a temperature of 28° C.

Compared with untreated test samples, a pronounced inhibition of growth is found.

What is claimed is:

1. A hydroxyphenyl ketone of the formula:

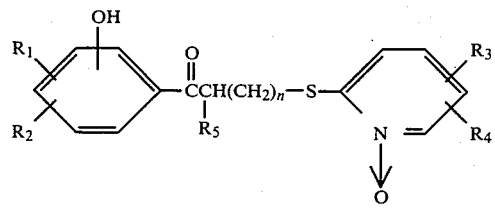

in which n is the number 0, 1, 2 or 3, wherein the hydroxyl group is in the 3-position only when n is 0 or 1, $R_1$ and $R_2$ independently of one another are hydrogen, fluorine, chlorine, bromine, nitro, methyl or methoxy, $R_3$ is hydrogen, chlorine, bromine, methyl or methoxy, $R_4$ is hydrogen, chlorine, bromine or methyl, and $R_5$ is hydrogen or, if n is 1, a group of the formula:

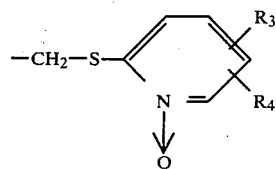

in which $R_3$ and $R_4$ are as defined above.

2. A hydroxyphenyl ketone of claim 1, wherein $R_2$, $R_4$ and $R_5$ are hydrogen.

3. A hydroxyphenyl ketone of claim 2, wherein the hydroxyl group is in the 2-position and $R_3$ is hydrogen, chlorine, bromine or methyl.

4. A hydroxyphenyl ketone of claim 3, wherein $R_1$ is hydrogen, chlorine, bromine, nitro or methyl.

5. A hydroxyphenyl ketone of claim 1, wherein $R_2$ and $R_4$ are hydrogen, $R_3$ is hydrogen, chlorine, bromine or methyl, the hydroxy group is ortho to the keto-group, and n is 1.

6. A hydroxyphenyl ketone of claim 5, wherein $R_1$ and $R_3$ are each independently hydrogen, chlorine or methyl.

7. A hydroxyphenyl ketone of claim 1, wherein the hydroxyl group is in the 2-position, n is 1, $R_2$ and $R_5$ are hydrogen and $R_1$, $R_3$ and $R_4$ are each independently hydrogen, chlorine or methyl.

8. A hydroxyphenyl ketone of claim 1, wherein the hydroxyl group is in the 2-position, n is 0, $R_2$ and $R_5$ are hydogen, and $R_1$, $R_3$ and $R_4$ are each independently hydrogen, chlorine or methyl.

9. An anti-microbial composition comprising an inert carrier and an effective amount of a hydroxyphenyl ketone of claim 1.

10. A method for combating micro-organisms on or in an organic substrate and for protecting said substrate against micro-organisms, comprising the step of incorporating in or applying to the surface of said substrate an effective amount of a hydroxyphenyl ketone of claim 1.

* * * * *